US012752058B2

(12) United States Patent
Chuvashova

(10) Patent No.: US 12,752,058 B2
(45) Date of Patent: *Oct. 6, 2026

(54) MEDICAMENT DELIVERY DEVICE

(71) Applicant: SHL MEDICAL AG, Zug (CH)

(72) Inventor: Natalia Chuvashova, Nacka (SE)

(73) Assignee: SHL Medical AG, Zug (CH)

( * ) Notice: Subject to any disclaimer, the term of this patent is extended or adjusted under 35 U.S.C. 154(b) by 483 days.

This patent is subject to a terminal disclaimer.

(21) Appl. No.: 18/528,050

(22) Filed: Dec. 4, 2023

(65) Prior Publication Data

US 2024/0100261 A1 Mar. 28, 2024

Related U.S. Application Data

(63) Continuation of application No. 16/950,635, filed on Nov. 17, 2020, now Pat. No. 11,872,380, which is a (Continued)

(30) Foreign Application Priority Data

Mar. 12, 2013 (SE) .................................... 1350292-7

(51) Int. Cl.
*A61M 5/31* (2006.01)
*A61M 5/315* (2006.01)

(52) U.S. Cl.
CPC .... *A61M 5/31566* (2013.01); *A61M 5/31585* (2013.01); *A61M 5/31535* (2013.01); *A61M 5/31553* (2013.01); *A61M 2205/19* (2013.01)

(58) Field of Classification Search
CPC ............ A61M 5/3155; A61M 5/31551; A61M 5/31553; A61M 5/31585
See application file for complete search history.

(56) References Cited

U.S. PATENT DOCUMENTS 4,865,591 A 9/1989 Sams
5,279,585 A 1/1994 Balkwill
(Continued)

FOREIGN PATENT DOCUMENTS

WO 2005/097240 A1 10/2005
WO 2008/116766 A1 10/2008
(Continued)

OTHER PUBLICATIONS

EPO, Int'l Search Report in PCT/EP2014/054209, Jun. 20, 2014.
EPO, Written Opinion in PCT/EP2014/054209, Jun. 20, 2014.

*Primary Examiner* — William R Carpenter
(74) *Attorney, Agent, or Firm* — McDonnell Boehnen Hulbert & Berghoff LLP

(57) ABSTRACT

The present invention relates to a medicament delivery device for delivering a number of predetermined amounts of medicament, comprising a body having a proximal and an opposite distal end and extending along a longitudinal axis (L); a medicament container (20) arranged inside said body; a driving mechanism arranged inside said body and configured to act on said medicament container; a manually movable activation member (102) arranged on the distal end the body; a biased actuator member (64) arranged to be movable along the longitudinal axis and through the manually movable activation member (102), said biased actuator member being configured to protrude a predetermined distance from the distal end of the manually movable activation member and configured to interact with said driving mechanism when the biased actuator member is displaced said predetermined distance towards the proximal end of the body for delivering a predetermined amount of medicament; and an actuator guide member (90) arranged in the body and configured to interact with the manually movable activation member (102) and with the biased actuator member (64) such that said actuator guide member (90) can be held in a (Continued)

position within the body and released from said position after a predetermined amount of medicament is delivered; wherein the actuator guide member (90) comprises at least one second guide element (92) adapted to interact with blocking surfaces in at least one group of guide surfaces (76) arranged on the outer circumferential surface of the biased actuator member (64) if said biased actuator member is operated towards the proximal end of the body during displacement of the biased actuator member (64) from the distal end of the manually movable activation member or if said biased actuator member is released during displacement of the biased actuator member (64) towards the proximal end of the body.

16 Claims, 17 Drawing Sheets

Related U.S. Application Data continuation of application No. 14/774,847, filed as application No. PCT/EP2014/054209 on Mar. 5, 2014, now Pat. No. 10,881,807.

(60) Provisional application No. 61/777,364, filed on Mar. 12, 2013.

(56) References Cited

U.S. PATENT DOCUMENTS

| | | | | |
|---|---|---|---|---|
| 5,925,021 | A | 7/1999 | Castellano et al. | |
| 9,180,255 | B2 | 11/2015 | Kouyoumjian et al. | |
| 10,881,807 | B2 * | 1/2021 | Chuvashova | A61M 5/31566 |
| 11,872,380 | B2 * | 1/2024 | Chuvashova | A61M 5/31566 |
| 2005/0137534 | A1 | 6/2005 | Hommann | |
| 2009/0259181 | A1 | 10/2009 | Moser | |
| 2010/0036320 | A1 | 2/2010 | Cox et al. | |
| 2010/0114025 | A1 * | 5/2010 | Moller | A61M 5/31533 604/135 |
| 2013/0218098 | A1 | 8/2013 | Chung | |
| 2014/0039410 | A1 * | 2/2014 | Harms | A61M 5/3155 604/218 |

FOREIGN PATENT DOCUMENTS

| | | | |
|---|---|---|---|
| WO | 2009/080775 | A1 | 7/2009 |
| WO | 2009/097934 | A1 | 8/2009 |
| WO | 2011/152772 | A1 | 12/2011 |

* cited by examiner

MEDICAMENT DELIVERY DEVICE

CROSS REFERENCE TO RELATED APPLICATIONS

The present application is a continuation of U.S. patent application Ser. No. 16/950,635 filed Nov. 17, 2020, which is a continuation of U.S. patent application Ser. No. 14/774,847 filed Sep. 11, 2015, now U.S. Pat. No. 10,881,807, which is a U.S. National Phase Application pursuant to 35 U.S.C. § 371 of International Application No. PCT/EP2014/054209 filed Mar. 5, 2014, which claims priority to U.S. Provisional Patent Application No. 61/777,364 filed Mar. 12, 2013 and Swedish patent application Ser. No. 1350292-7 filed Aug. March 12, 2013. The entire disclosure contents of these applications are herewith incorporated by reference into the present application.

TECHNICAL FIELD

The present invention relates to a medicament delivery device and in particular to a robust device comprising enhanced dose delivery features.

BACKGROUND OF INVENTION

Basically a medicament delivery device is a device that is simple to use without the need of performing many steps when an individual has to administer a dose of medicament by himself/herself. This requires a solution able of keeping a medicament delivery device as pre-assembled and ready as possible, in order to deliver the medicament in a measured dosage, without many manual operations or actions. Thus, to minimize the number of steps needed, in order to perform a medicament delivery, some known prior art devices only need to be actuated against the delivery area, without the need of manual actuation, by pressing a button or the like, which causes the medicament delivery device to perform the delivery. There is however a common request for a medicament delivery device which is very easy to use and which can reliably deliver a set dose of a medicament in a safe way.

U.S. Pat. No. 5,925,021 discloses a pen injector device comprising a locking means for locking the actuator knob in a depressed position, a start button for releasing the actuator button and a dosage knob for setting a prescribed dose. U.S. Pat. No. 5,925,021 also comprises electronics, such as sensors and display devices for controlling the injection, for measuring and storing ejected doses and for displaying information to the user. A disadvantage of this prior art is that a dose needs to be set and then injected manually by pushing the actuator button until it stops. In a stressful situation, or if handled by an inexperienced user, the injection may be interrupted mid-way and the button may be released inadvertently. If the button is depressed again, i.e. without adjusting the dosage, a new dose of the previous setting will be initialized, which will lead to the patient receiving an overdose.

One solution that addresses the above problems is disclosed in WO2011/152772. The solution comprises a medicament delivery device that comprises a manually operated push means movable in the longitudinal direction and capable, upon operation, of moving a plunger rod for expelling medicament. The push means is operably connected to a moveable release member with a guide member, in turn operably arranged to a guide frame. The guide frame is arranged with a number of guide surfaces and flexible protrusions that are configured to prevent delivery of a subsequent dose before a previously initialized dose has been fully administered.

The solution according to WO2011/152772 works well for most users. However, in order to prevent that a new full dose of medicament is given if the user disrupts a dose delivery sequence e.g. half way, by releasing the push means and subsequently pressing on the push means again, the guide member passes a flexible non-return protrusion during the dose delivery sequence. The passing of the flexible non-return protrusion causes an audible and tactile signal that may be confusing for some users, where they might believe that the dose delivery sequence has ended, even though only half of the dose might have been delivered.

There is therefore a need for an arrangement that can provide a robustness, safe and simple handling both by inexperienced users and in stressful situations. Hence, there is a need for an arrangement where a predetermined dosage is fully delivered without any miss-leading information. Thus, as can be noted, human handling aspects of the medicament delivery device are crucial and there are several rationales for improving existing solutions

BRIEF DESCRIPTION OF INVENTION

In the present application, when the term “distal” is used, this refers to the direction pointing away from the dose delivery site. When the term “distal part/end” is used, this refers to the part/end of the delivery device, or the parts/ends of the members thereof, which under use of the medicament delivery device is/are located furthest away from the dose delivery site. Correspondingly, when the term “proximal” is used, this refers to the direction pointing to the dose delivery site. When the term “proximal part/end” is used, this refers to the part/end of the delivery device, or the parts/ends of the members thereof, which under use of the medicament delivery device is/are located closest to the dose delivery site.

Further, the term “longitudinal”, with or without “axis”, refers to a direction or an axis through the device or components thereof in the direction of the longest extension of the device or the component. In a similar manner, the term “lateral”, with or without “axis”, refers to a direction or an axis through the device or components thereof in a direction generally perpendicular to the longitudinal direction. Also, if nothing else is stated, in the following description wherein the mechanical structure of the device and the mechanical interconnection of its components is described, the device is in an initial non-activated or non-operated state.

The aim of the present invention is to remedy the drawbacks of the state of the art medicament delivery devices. This aim is solved by a device according to the features of the independent patent claim. Preferable embodiments form the subject of the dependent patent claims.

The medicament delivery device according to the present invention is designed for delivering a number of predetermined amounts of medicament. It may comprise a body having a proximal and an opposite distal end and extending along a longitudinal axis (L). The body comprises a proximal housing part and a distal housing part and having a proximal and an opposite distal end. The body is arranged to accommodate a medicament container with medicament to be delivered to a patient. The medicament container preferably comprises a movable stopper and an opening for expelling medicament. To the opening, a suitable medicament delivery member may be attached or integrated, where the medicament delivery member may comprise for example an injection needle, a mouthpiece, a nebulizing nozzle or the like. Preferably, the medicament container is arranged inside said proximal housing part.

The device may further comprise a driving mechanism arranged inside said body and configured to act on said medicament container.

The device may also comprise a manually movable activation member arranged on the distal end the body and wherein said manually movable activation member is movable arranged in relation to the body, more particularly, rotatable in relation to the body.

The medicament delivery device may preferably also comprise a biased actuator member arranged to be movable along the longitudinal axis and through the manually movable activation member, said biased actuator member being configured to protrude a predetermined distance from the distal end of the manually movable activation member and configured to interact with said driving mechanism when the biased actuator member is displaced said predetermined distance towards the proximal end of the body for delivering a predetermined amount of medicament.

The device may further comprise an actuator guide member arranged in the body and configured to interact with the manually movable activation member and with the biased actuator member such that said actuator guide member can be held in a position within the body and released from said position after a predetermined amount of medicament is delivered.

According to a preferable solution of the present invention, the actuator guide member comprises at least one second guide element adapted to interact with blocking surfaces in at least one group of guide surfaces arranged on the outer circumferential surface of the biased actuator member if said biased actuator member is operated towards the proximal end of the body during displacement of the biased actuator member from the distal end of the manually movable activation member or if said biased actuator member is released during displacement of the biased actuator member towards the proximal end of the body.

In this manner it is ascertained that the device is robust and cannot miss-deliver a predetermined amount of medicament. A delivery operation may be interrupted by a user but a subsequent predetermined amount of medicament cannot be delivered until the previous predetermined amount of medicament has been completely delivered. This is because the device cannot be reset or initialized for a subsequent predetermined amount of medicament without completely depressing the biased actuator member for total delivery of the current predetermined amount of medicament. Also, the device cannot be handled in a wrong way by a user unintentionally operating on the biased actuator member during release of the biased actuator member. This is an important feature since if a user would press the biased actuator member without a blocking surface preventing movement of said biased actuator member in a proximal direction, an inaccurate predetermined amount of medicament would be delivered.

Further, the driving mechanism comprises: a threaded plunger rod arranged in contact with said movable stopper and a transforming mechanism capable of transforming the displacement of said predetermined distance towards the proximal end of the body of said biased actuator member to a rotational movement of said threaded plunger rod. The transforming mechanism comprises:—a first driver which is rotatably locked to said threaded plunger rod and which comprises a first set of protruding structures, and—a second driver having a set of inclined surfaces and a second set of protruding structures; such that when said biased actuator member is displaced said predetermined distance towards the proximal end of the body, said second set of protruding structures interacts with a corresponding set of protruding structures of the biased actuator member and said first set of protruding structures interacts with said set of inclined surfaces arranged on said second driver.

The device further comprises a spring means for biasing said biased actuator member a distal direction from the distal end of the manually movable activation member and the actuator guide member further comprises at least one first guide element adapted to interact with a corresponding at least one third guide element of said manually movable activation member, such that when said manually movable activation member is manually operated, the at least one third guide element of said manually movable activation member interact with the at least one first guide element of said actuator guide member so that the at least one second guide element is moved along said at least one group of guide surfaces whereby said biased actuator member is moved by said spring means in a distal direction from the distal end of the manually movable activation member for setting the device ready for delivery. The distal movement of the biased actuator member may preferably be at a distal end of the device, such that the biased actuator member may be subsequently operated by e.g. a thumb of a user when a predetermined amount of medicament is to be delivered through a medicament delivery member. This also indicates to a user that the device is ready for use. I.e. before operation of the manually movable activation member, the biased actuator member may be hidden or depressed into the body of the device.

Guide surfaces are also a convenient ways of handling the interaction and functions of different components in a medicament delivery device. According to the preferable embodiment of the invention, the at least one second guide element interacts and moves along the guide surfaces in order to hold and release the biased actuator member from a locked position. According to a further preferable embodiment of the invention, one of the blocking surfaces in at least one group of guide surfaces arranged on the outer circumferential surface of the biased actuator member is a first blocking surface configured to interact with the at least one second guide element for preventing manual operation of said biased actuator member towards the proximal end of the body during movement of the biased actuator member in a distal direction from the distal end of the manually movable activation member. Again, in this manner it is ascertained that the device cannot be handled in a wrong way by a user unintentionally operating on the biased actuator member during release of the biased actuator member. This is an important feature since if a user would press the biased actuator member without a surface preventing movement of said biased actuator member in a proximal direction an incomplete predetermined amount of medicament would be delivered.

In this respect, one of the blocking surfaces in at least one group of guide surfaces arranged on the outer circumferential surface of the biased actuator member is a second blocking surface configured to interact with the at least one second guide element for preventing movement of said biased actuator member in a distal direction from the distal end of the manually movable activation member if said biased actuator member is released during delivery such that the delivery of a subsequent predetermined amount of medicament before a previous predetermined amount of medicament has been fully administered is prevented. This is an important feature since if a user would release the biased actuator member without a surface preventing movement of said biased actuator member in a distal direction from the distal end of the manually movable activation member, the biased actuator member would again extend the predetermined distance in the distal direction, whereby a subsequent predetermined amount of medicament would be delivered in addition to the previous partial amount of medicament.

In other words, the biased actuator member comprises at least one group of guide surfaces arranged on the outer circumferential surface of the biased actuator member, wherein the at least one group of guide surfaces comprises a first blocking surface adapted to interact with at least one second guide element of the actuator guide member if said biased actuator member is operated towards the proximal end of the body during displacement of the biased actuator member from the distal end of the manually movable activation member and wherein the at least one group of guide surfaces further comprises a second blocking surface adapted to interact with the at least one second guide element of the actuator guide member if said biased actuator member is released during delivery such that the delivery of a subsequent predetermined amount of medicament before a previous predetermined amount of medicament has been fully administered is prevented.

According to another preferable solution of the present invention, the biased actuator member further comprises at least one lock element engageable with said at least one second guide element for locking said biased actuator member in a position when a predetermined amount of medicament has been delivered. In this manner the biased actuator member is locked and no more predetermined amounts of medicament may be performed until the device is again activated. The locking of the biased actuator member also indicates that the device has been used and is not yet ready for a subsequent delivery of predetermined amount of medicament. Preferably the indication that the device has been used is when the biased actuator member in a position moved into said body. In addition to the locking function of the at least one lock element, it may also be arranged to produce an audible signal when locking said biased actuator member. This gives a positive feedback to the user that the device may be removed from the dose delivery site. In addition to the audible signal, a tactile signal may also be provided in that the at least one lock element is arranged as a flexible tongue that flexes rapidly when the at least one second guide element is contacting the lock element, such that the at least one lock element strikes a surface of the device, producing a vibration thereof.

Preferably the manually movable activation member is arranged turnable on said body and configured to turn said actuator guide member when said manually movable activation member is turned in relation to the body.

Further, the at least one group of guide surfaces are configured to turn said actuator guide member when said biased actuator member is displaced along the longitudinal axis and in relation to the body.

According to a preferable solution of the present invention, by having a manually movable activation member and an actuator guide member operably connected to the body and operably interconnected to each other, the release of said biased actuator member, when the manually movable activation member is operated, may cause a disconnection of the actuator guide member from the manually movable activation member. This ensures that the turning of the actuator guide member during operation of the device is not affected or hindered by a user being in contact with the manually movable activation member. Otherwise, if the manually movable activation member and the actuator guide member are in one piece, then a contact by the user of the activation mechanism could prevent the turning of the actuator guide member and could thus prevent proper function of the device. This solution offers a reliable and robust device.

These and other features of the present invention and advantages thereof will become apparent from the following detailed description of the invention and from the accompanying drawings.

BRIEF DESCRIPTION OF THE DRAWINGS

In the following detailed description of the invention, reference will be made to the accompanying drawings, of which

DETAILED DESCRIPTION OF THE INVENTION

Figure 1:
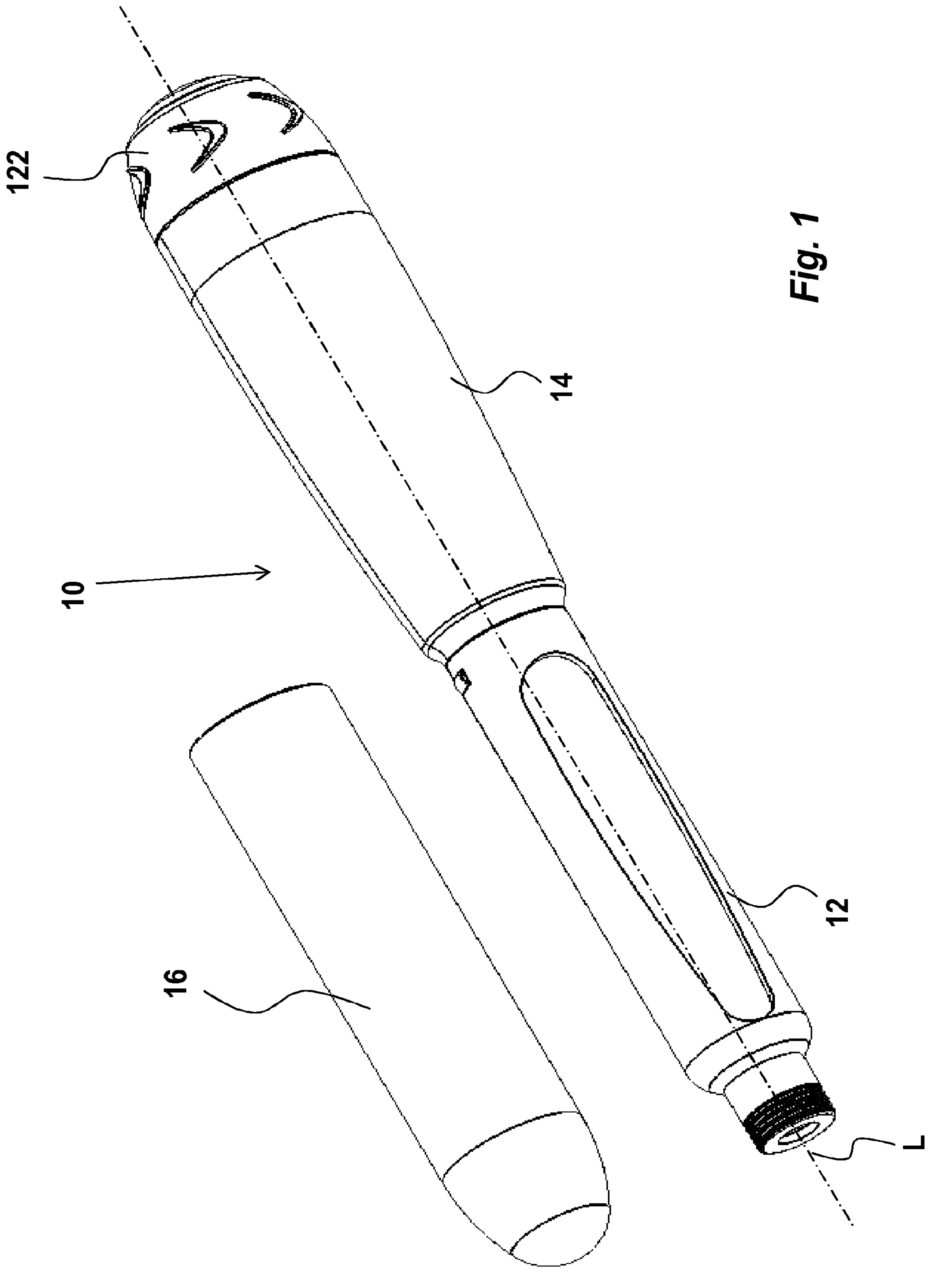
FIG. 1 shows an embodiment of a medicament delivery device according to the present invention.

The embodiment of a medicament delivery device shown in the drawings comprises an elongated body 10 having a proximal and an opposite distal end and extending along a longitudinal axis (L), FIG. 1. The body 10 comprises a proximal housing part 12 and a distal housing part 14. In the embodiment shown the distal housing part is arranged as two halves $\mathbf{14}^{I}$, $\mathbf{14}^{II}$, FIG. 2, but it is to be understood that there may be other housing arrangements within the scope of the invention. For instance, the device according to the embodiment shown is arranged with a protective cap 16, FIG. 1, that is capable of covering at least a part of the proximal housing part 12 and its proximal end.

Figure 2:
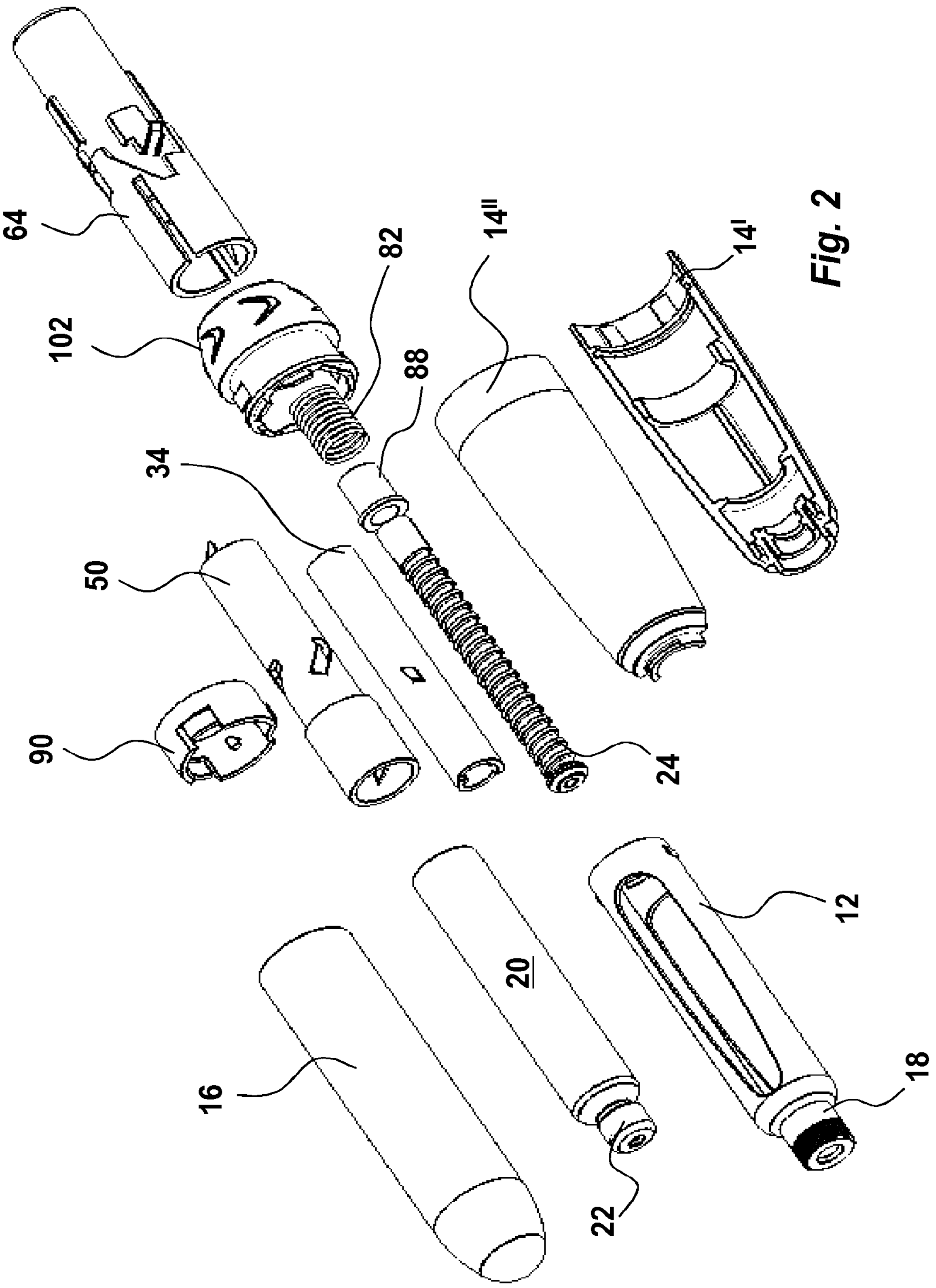
FIG. 2 shows an exploded view of the embodiment of FIG. 1.
Figure 3:
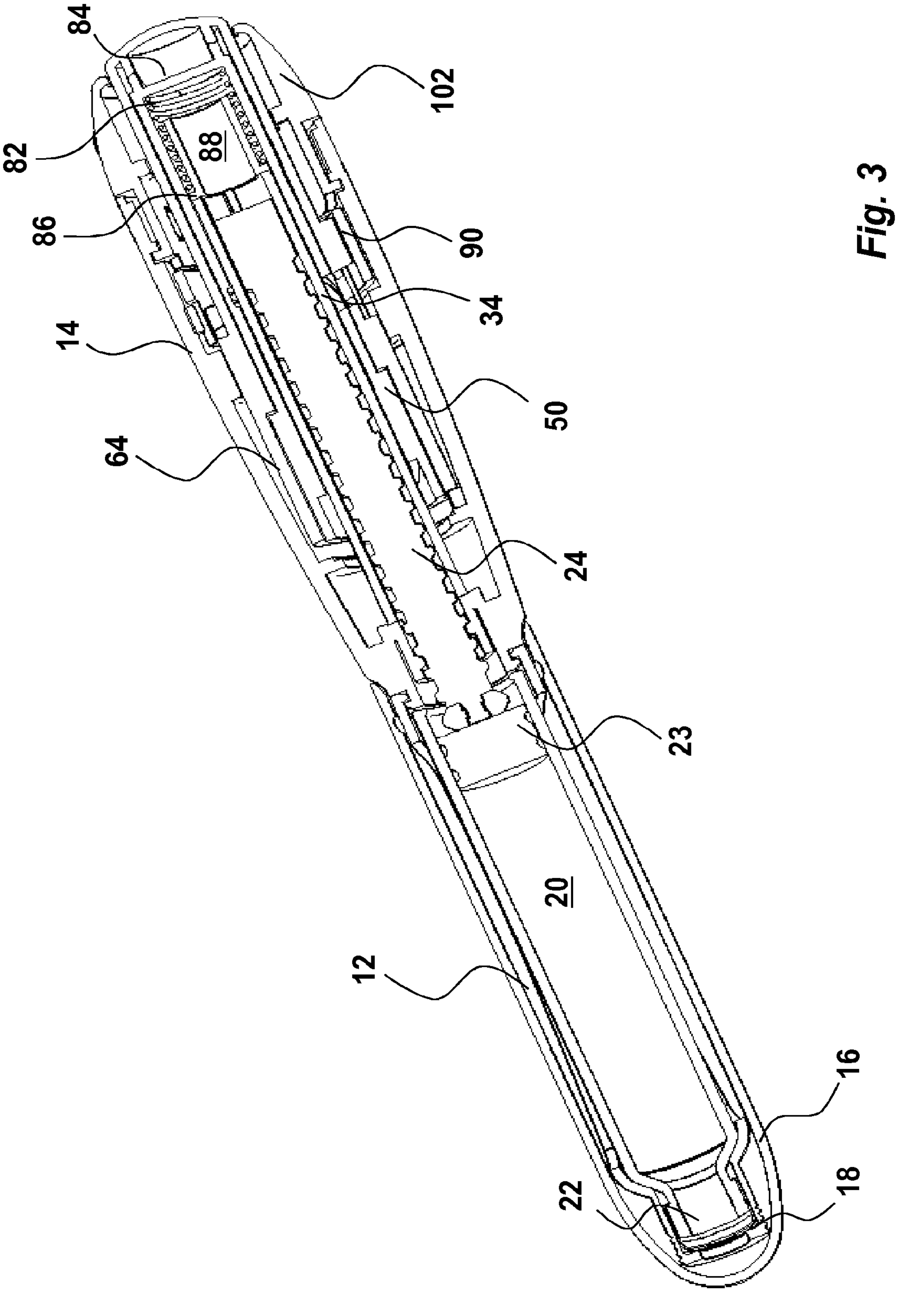
FIG. 3 shows a cross-sectional view of the embodiment of FIG. 1, FIGS. 4-9 show detailed views of components comprised in the embodiment of FIG. 1, and FIGS. 10-17 show different functional views of the embodiment of FIG. 1.

The proximal housing part 12 is provided with a neck portion 18, FIG. 2, which neck portion 18 is arranged with attachment members, such as threads, on which a medicament delivery member (not shown) may be attached. The proximal housing part 12 is further arranged to accommodate a medicament container 20 having a generally tubular shape and arranged with a proximal neck portion 22 arranged to fit into the neck portion of the proximal housing part 12, as seen in FIG. 3. The neck portion 22 of the medicament container 20 is arranged with a penetrable septum, through which a medicament delivery member, such as an injection needle may extend for delivering a dose of medicament from the container. At a distal area of the medicament container, a stopper 23, FIG. 3, is arranged movable in the longitudinal direction.

A driving mechanism is further arranged inside said body and configured to act on said medicament container. Also, a manually movable activation member 102 is arranged on the distal end the body.

The device further comprises a biased actuator member 64 arranged to be movable along the longitudinal axis and through the manually movable activation member 102, said biased actuator member being configured to protrude a predetermined distance from the distal end of the manually movable activation member and configured to interact with said driving mechanism when the biased actuator member is displaced said predetermined distance towards the proximal end of the body for delivering a predetermined amount of medicament.

Figure 4:
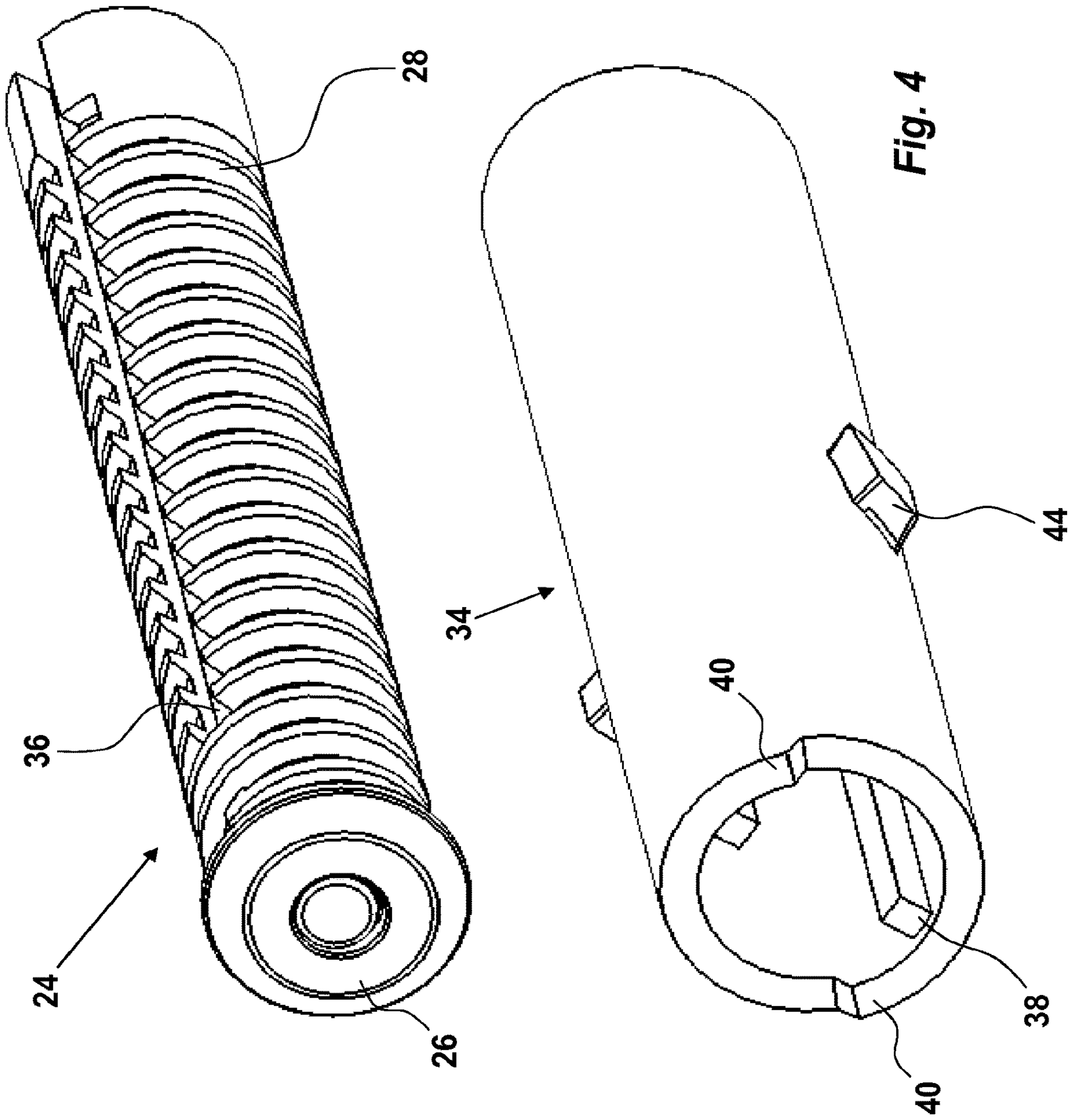
Figure 5:
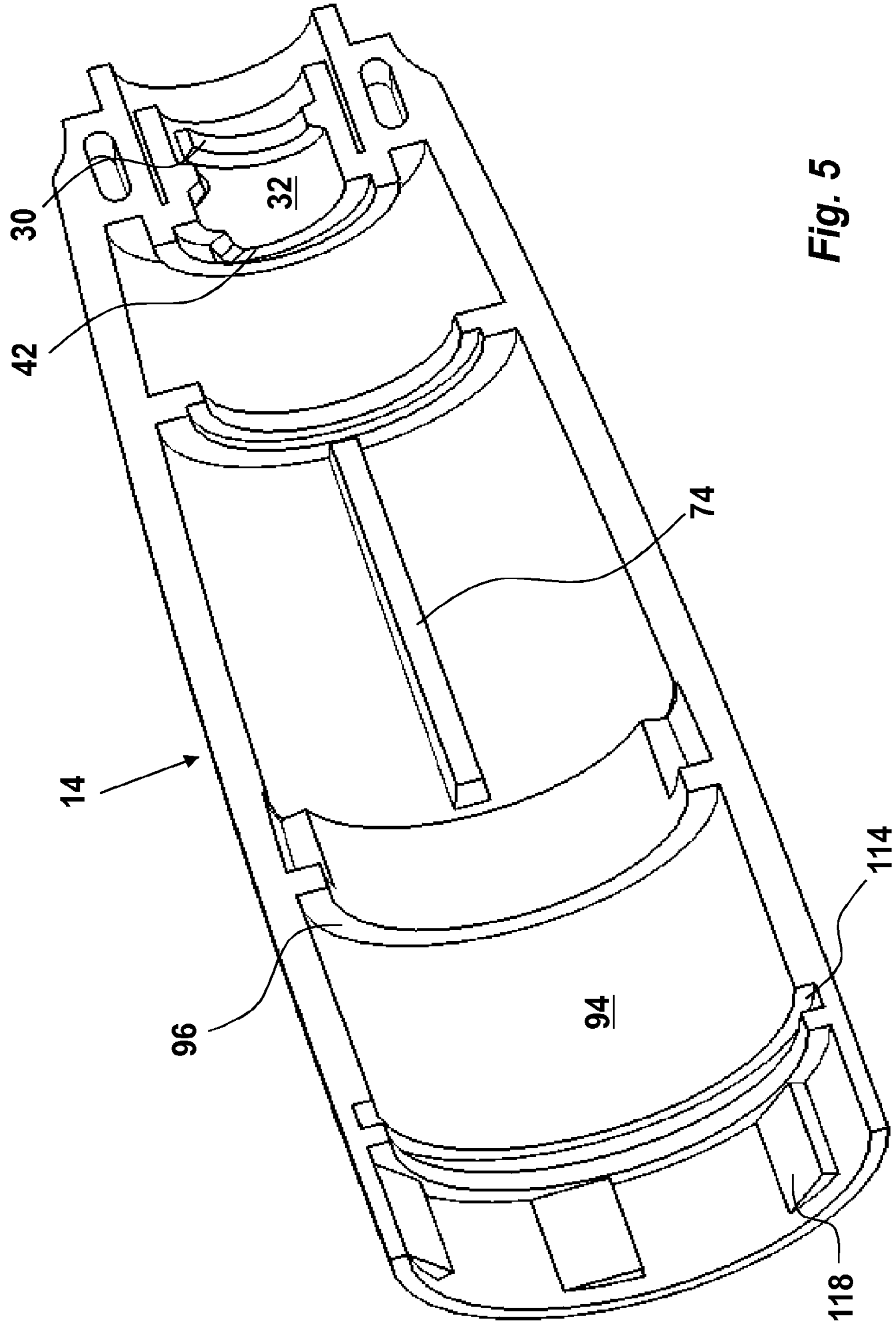

The driving mechanism comprises a threaded plunger rod 24, FIGS. 2 to 4, arranged in contact with said movable stopper 23, and a transforming mechanism capable of transforming the displacement of said predetermined distance towards the proximal end of the body of said biased actuator member 64 to a rotational movement of said plunger rod 24. The proximal end of the plunger rod 24 may be arranged with a rotatable spinner 26, FIG. 4. The threaded plunger rod 24 is arranged with threads 28, FIG. 4, that are arranged to cooperate with corresponding thread segments 30 arranged in a central passage 32 in the distal housing part 14, FIG. 5.

The transforming mechanism comprises a first driver 34 which is rotatably locked to said plunger rod 24 and which comprises a first set of protruding structures 44, and a second driver 46 having a set of inclined surfaces 54 and a second set of protruding structures 62.

Figure 6:
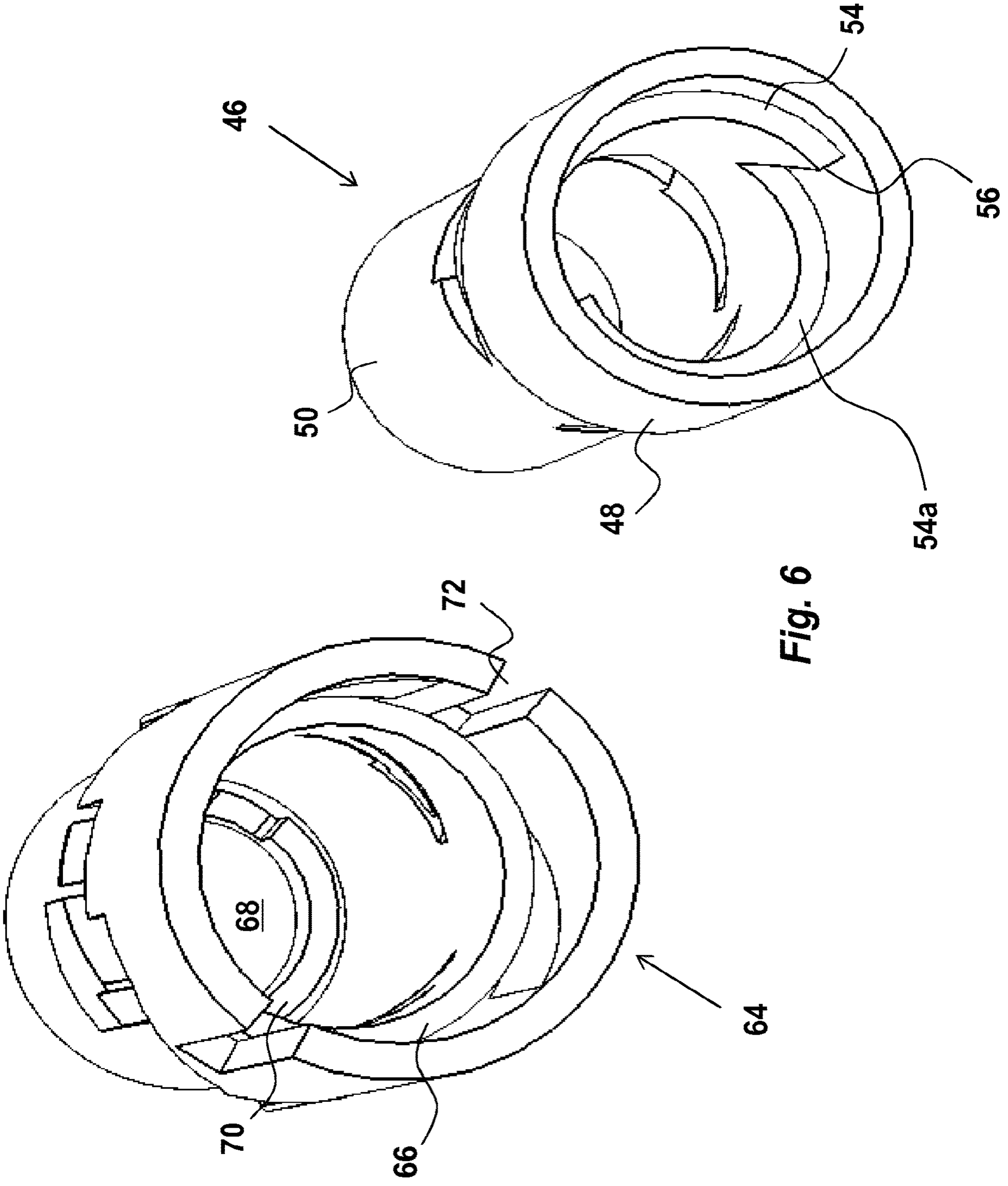
Figure 8:
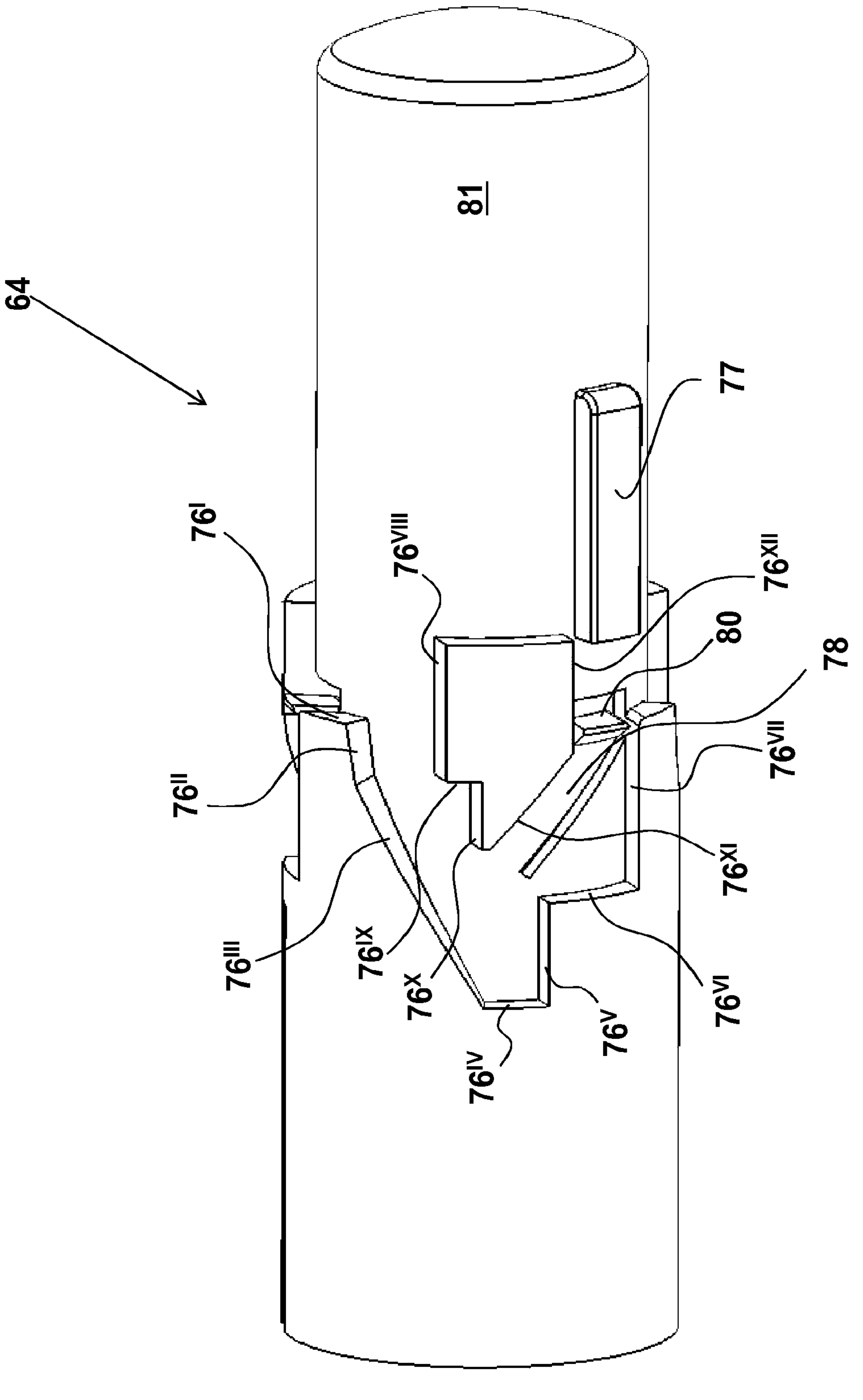

The biased actuator member 64, FIGS. 6 and 8, is arranged to interact with the second driver 46. The biased actuator member 64 is arranged as a generally tubular body having an interior with two different diameters such that the second driver 46 may fit into the biased actuator member 64. In this respect, the biased actuator member 64 is arranged with a proximally directed circumferential ledge 66, FIG. 6, arranged to be in contact with the distally directed ledge 52 of the second driver 46.

At the distal end of the second driver 46 an end wall 60 is arranged. The end wall 60 is arranged with the second set of protruding structures 62 wherein in the embodiment shown said second set of protruding structures 62 is e.g. two wedge-shaped protrusions, FIG. 7, extending in the distal direction.

The biased actuator member 64 is further arranged with an end wall 68 at its distal end. The end wall 68 is arranged with a ratchet 70, FIG. 6, designed to interact with the second set of protruding structures 62 of the second driver 46, as will be described below. The biased actuator member 64 is further arranged with at least one group of specifically designed guide surfaces 76 on its outer surface, FIG. 8.

Further, in the present embodiment, a proximal area of the biased actuator member 64 is arranged with a number of longitudinally extending grooves or cut-outs 72, FIG. 6. These cut-outs 72 are intended to interact with a number of longitudinally extending ribs 74, FIG. 5, on inner surfaces of the housing 14 such that a rotational lock is obtained, but allowing longitudinal movement between them.

When said biased actuator member 64 is displaced said predetermined distance towards the proximal end of the body, said second set of protruding structures 62 of the second driver 46 interacts with a corresponding set of protruding structures of the biased actuator member 64 and said first set of protruding structures 44 of the first driver 34 interacts with said set of inclined surfaces 54 arranged on said second driver 46.

The first driver 34, FIG. 4, is surrounding the threaded plunger rod 24, wherein the diameter of the threaded plunger rod 24 is somewhat smaller than the inner diameter of the driver 34. In the present embodiment, the threaded plunger rod 24 is arranged with a number of longitudinally extending grooves 36 and the first driver 34 is arranged with a corresponding number of longitudinally extending ridges 38, fitting into the grooves 36 such as to obtain a rotational lock between the two components, while allowing longitudinal movement between them. A proximally directed circumferential end surface of the first driver 34 is arranged with inclined wedge-shaped surface areas 40, FIG. 4, which are intended to cooperate with correspondingly shaped surface areas 42 on a distally directed circumferential surface on the distal housing part 14 surrounding the central passage 32, FIG. 5. Further, in the shown embodiment the first set of protruding structures 44 of the first driver 34 is e.g. a number of generally radially extending protrusions. Said first set of protruding structures 44 are arranged on the outer cylindrical surface of the first driver 34, FIG. 4.

Figure 7:
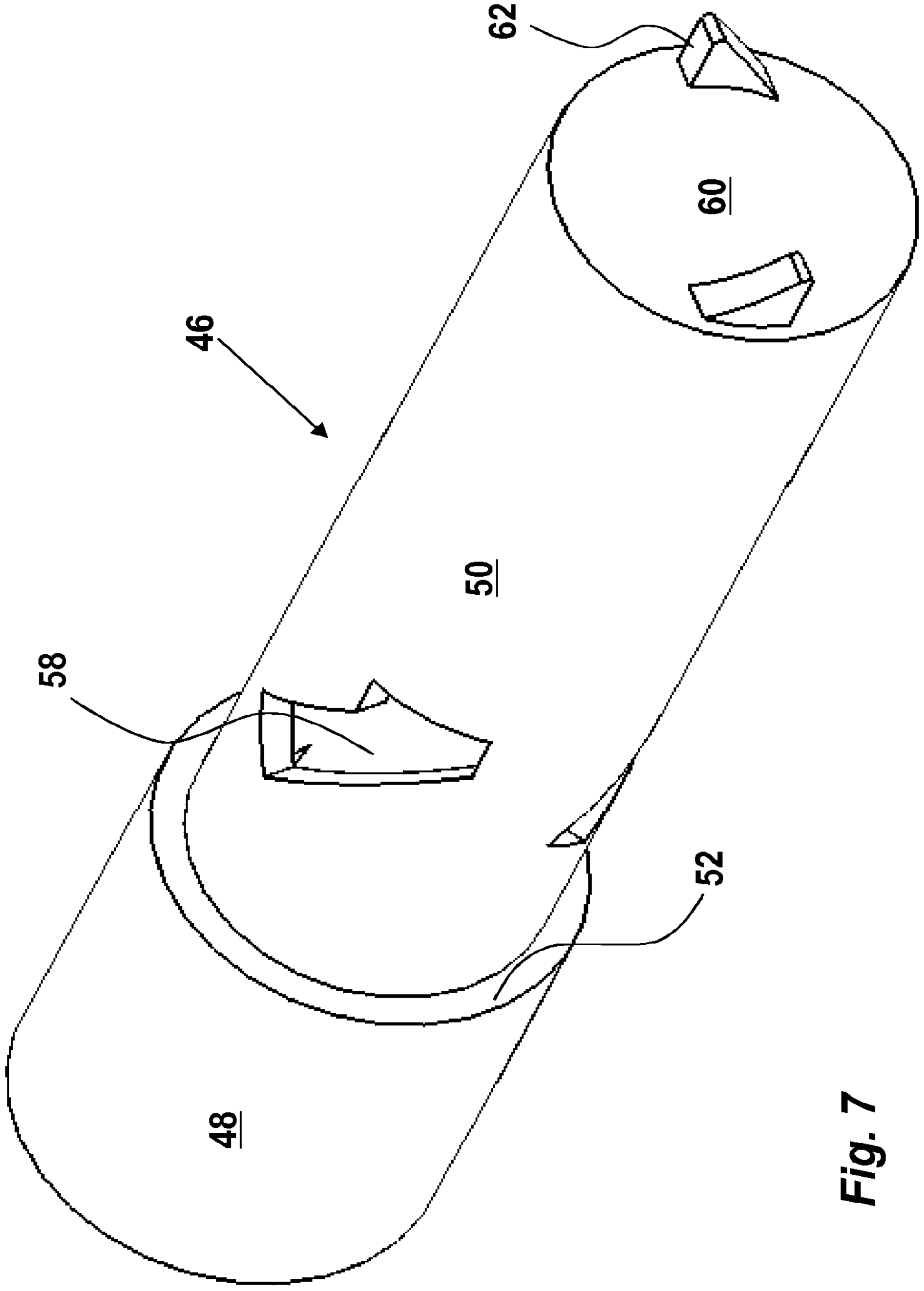

The set of inclined surfaces 54 is arranged on the inner surface of the second driver and in the in the shown embodiment, the set of inclined surfaces 54 is e.g. proximally directed inclined ledges, FIGS. 6 and 7. The second driver 46 further comprises a proximal part 48 with a first diameter and a distal part 50 having a second diameter, which is less than the first diameter. The proximal part 48 and the distal part 50 are separated by a distally directed circumferential ledge 52. Further, the set of inclined surfaces 54 is arranged as two inclined ridges **54*a*, interconnected with generally longitudinally extending portions 56. The second driver 46 is further arranged with cut-outs 58, FIG. 7**, the function of which will be described below.

The device also comprises an actuator guide member 90 arranged in the body and configured to interact with the manually movable activation member 102 and with the biased actuator member 64 such that said actuator guide member 90 can be held in a position within the body and released from said position after a predetermined amount of medicament is delivered, the function of which will be described below.

The actuator guide member 90 comprises at least one second guide element 92 adapted to interact with blocking surfaces in at least one group of guide surfaces 76 arranged on the outer circumferential surface of the biased actuator member 64 if said biased actuator member is operated towards the proximal end of the body during displacement of the biased actuator member 64 from the distal end of the manually movable activation member or if said biased actuator member is released during displacement of the biased actuator member 64 towards the proximal end of the body. More particularly, the at least one group of guide surfaces 76 comprises a first blocking surface $\mathbf{76}^{IX}$ adapted to interact with at least one second guide element 92 of the actuator guide member 90 if said biased actuator member 64 is operated towards the proximal end of the body during displacement of the biased actuator member from the distal end of the manually movable activation member and wherein the at least one group of guide surfaces 76 further comprises a second blocking surface $\mathbf{76}^{VI}$ adapted to interact with the at least one second guide element 92 of the actuator guide member 90 if said biased actuator member 64 is released during delivery such that the delivery of a subsequent predetermined amount of medicament before a previous predetermined amount of medicament has been fully administered is prevented.

In the present embodiment, three groups of guide surfaces are shown. As shown in FIG. 8, each group comprises a first circumferentially extending guide surface $\mathbf{76}^{I}$. Connected to this is a first longitudinal guide surface $\mathbf{76}^{II}$ extending in the proximal direction, in turn transforming into an inclined guide surface $\mathbf{76}^{III}$. This surface ends in a second circumferentially extending guide surface $\mathbf{76}^{IV}$. A second longitudinal guide surface $\mathbf{76}^{V}$ is then extending in the distal direction. Connected to this is then a third circumferentially extending guide surface which is the second blocking surface $\mathbf{76}^{VI}$, and finally a third longitudinal guide surface $\mathbf{76}^{VII}$ extending in the distal direction. This surface is then connected to the first circumferentially extending guide surface $\mathbf{76}^{I}$ of a subsequent group.

The at least one group of guide surfaces 76 further comprises a sub-group in turn comprising a fourth longitudinal guide surface $\mathbf{76}^{VIII}$ extending in the proximal direction. It connects to a short fourth circumferentially extending guide surface which is the first blocking surface $\mathbf{76}^{IX}$, which in turn connects to a fifth longitudinally extending guide surface $\mathbf{76}^{X}$. Then an inclined guide surface $\mathbf{76}^{XI}$ is extending in the distal direction, in turn connecting to a sixth longitudinal guide surface $\mathbf{76}^{XII}$ extending in the distal direction.

The biased actuator member 64 also comprises at least one lock element 78 which is engageable with said at least one second guide element 92 for locking said biased actuator member 64 in a position when a predetermined amount of medicament has been delivered.

Along the inclined guide surface $\mathbf{76}^{XI}$, the at least one lock element 78 in the form of e.g. a flexible tongue is arranged in the wall surface of the biased actuator member 64 extending with the free end in the distal direction. The free end of the at least one lock element 78 is arranged with a generally wedge-shaped ledge 80, the function of which will be described below. A distal area of the biased actuator member constitutes a manual actuator 81, which is to be operated by a finger of a user, e.g. a thumb.

The biased actuator member 64 is further arranged with a number of longitudinally extending ledges 77 on its outer surface, FIG. 8, the function of which will be described below.

The device also comprises a spring means 82 for biasing said biased actuator member 64 in a distal direction from the distal end of the manually movable activation member 102. One end of the spring means 82 is abutting a proximally directed wall surface 84 of the biased actuator member 64, FIG. 3, and the other end of the spring means 82 is abutting a circumferential ledge 86 of a generally tubular spring guide 88, the body of which extends into the spring 82 as seen in FIG. 3. The proximally directed surface of the ledge 86 of the spring guide 88 is in contact with a distally directed end surface of the first driver 34. Preferably the material of the spring guide 88 is such as to reduce or minimize the friction between the spring guide 88 and the first driver 34.

The device further comprises an actuator guide member 90 operably connected to the body and to the manually movable activation member 102. The actuator guide member 90 comprises at least one first guide element 100 adapted to interact with a corresponding at least one third guide element 106 of said manually movable activation member 102. The actuator guide member 90 further comprises at least one second guide element 92 adapted to interact with the at least one group of guide surfaces 76 arranged on the outer circumferential surface of the biased actuator member 64.

Figure 9:
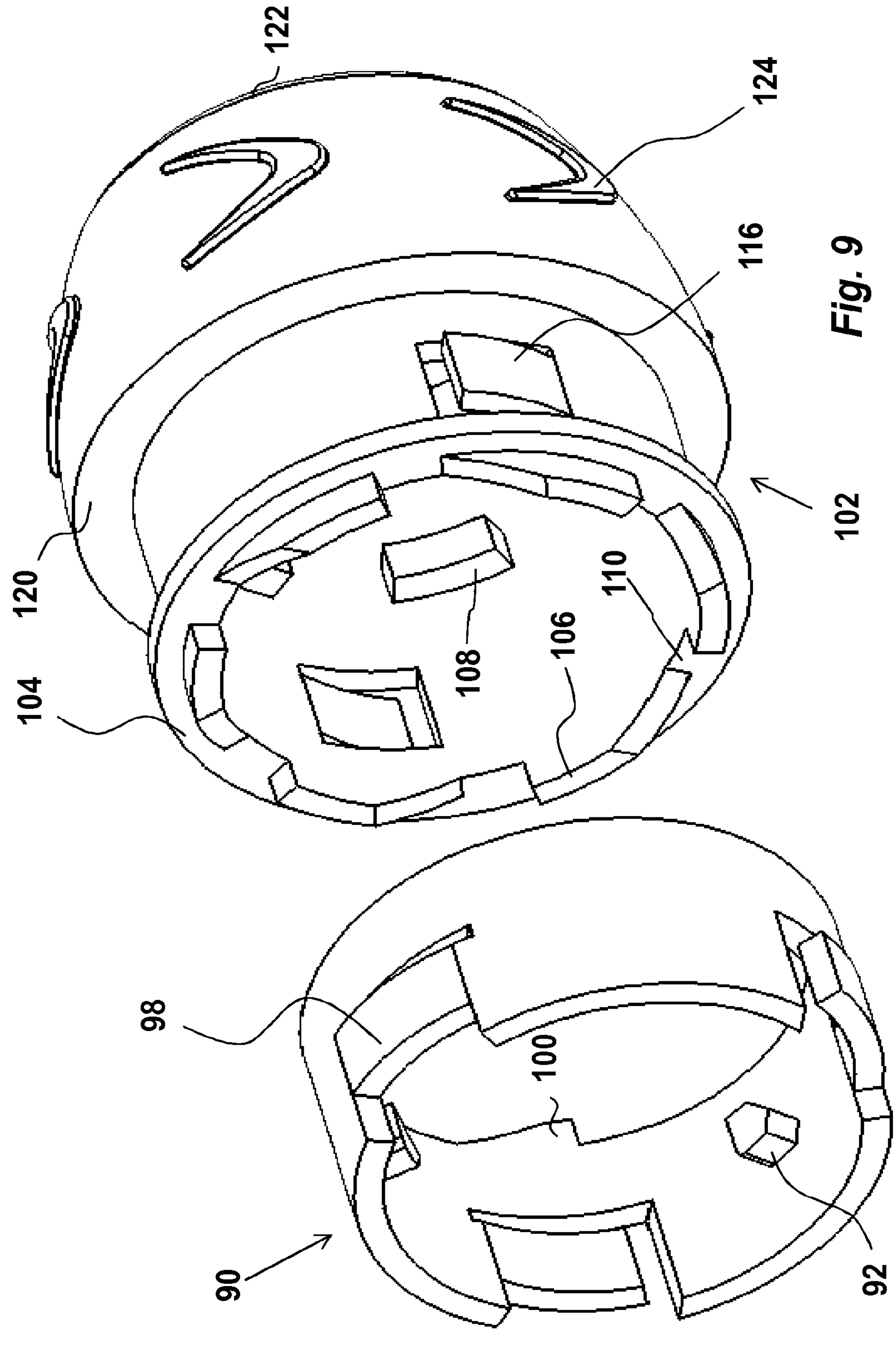

The actuator guide member 90 is a generally ring-shaped member, FIG. 9, and is positioned coaxially outside the biased actuator member 64 and movable in the distal housing part 14, more particularly, rotatable in relation to the distal housing part. The at least one second guide element 92 is arranged on the inner surface of the actuator guide member 90. The at least one second guide element 92 is shown as e.g. radially inwardly extending protrusions in the shown embodiment, FIG. 9. The number of second guide elements 92 corresponds to the number of groups of guide surfaces 76 of the biased actuator member 64. The at least one second guide element 92 is then arranged to cooperate with the guide surfaces 76 as will be described. The inner surface of the distal housing part 14 is provided with a seat 94 comprising a distally directed ledge 96, FIG. 5, for the actuator guide member 90, which seat 94 is arranged to allow rotational as well as longitudinal movement of the actuator guide member 90 as will be described.

The actuator guide member 90 is arranged with at least one generally radially flexible tongue 98, FIG. 9 arranged to act on the surfaces of the seat 94 to reduce or minimize any play between the actuator guide member 90 and the distal housing part 14. Further, a distally directed end surface of the actuator guide member 90 is arranged with the at least one first guide element 100, FIG. 9. In the shown embodiment, the at least one first guide element 100 is e.g. a protrusion arranged with an inclined surface and a generally longitudinally extending surface, giving the protrusion a wedge-shape.

The manually movable activation member 102 has a generally tubular shape, FIG. 9. A proximal end of the manually movable activation member 102, more particularly, a proximally directed surface of a circumferentially extending ledge 104 is arranged with the at least one third guide element 106. In the shown embodiment the at least one third guide element 106 is e.g. a proximally directed protrusion with an inclined surface. A space 110 is arranged between two adjacent third guide elements 106, FIG. 9. The at least one third guide element 106 is arranged to operably interact with the at least one first guide element 100 of the actuator guide member 90. The circumferentially extending ledge 104 of the manually movable activation member 102 is further intended to fit into a circumferential seat 114 of the distal housing part 14, FIG. 5.

In the present embodiment, adjacent the circumferentially extending ledge 104 a number of generally radially flexing tongues 116 are arranged, which tongues 116 extend in the circumferential direction of the manually movable activation member 102. The tongues 116 are arranged to interact with generally wedge-shaped protrusions 118, FIG. 5, on the inner surface of a distal end area of the distal housing part 14. Adjacent the generally radially flexing tongues 116, a number of radial inwardly extending protrusions 108 are arranged and wherein a number of spaces are formed between the radial inwardly extending protrusions 108, FIG. 9. The manually movable activation member 102 is further arranged with a proximally directed ledge 120 arranged to be in contact with a distally directed end surface of the distal housing part 14. The manually movable activation member 102 is further arranged with a grip member 122 positioned distally of the distal housing part as seen in FIG. 1. The grip member 122 may preferably be arranged with grip-enhancing members 124 on its outer surface.

The device is intended to function as follows. Preferably the device is arranged with a medicament container 20 placed in the proximal housing part 12 when delivered to a user. The proximal end of the device as well as its threaded neck portion are covered by the protective cap 16. When the device is to be used, the protective cap 16 is removed and a medicament delivery member (not shown) is attached to the proximal neck portion 18.

Figure 10:
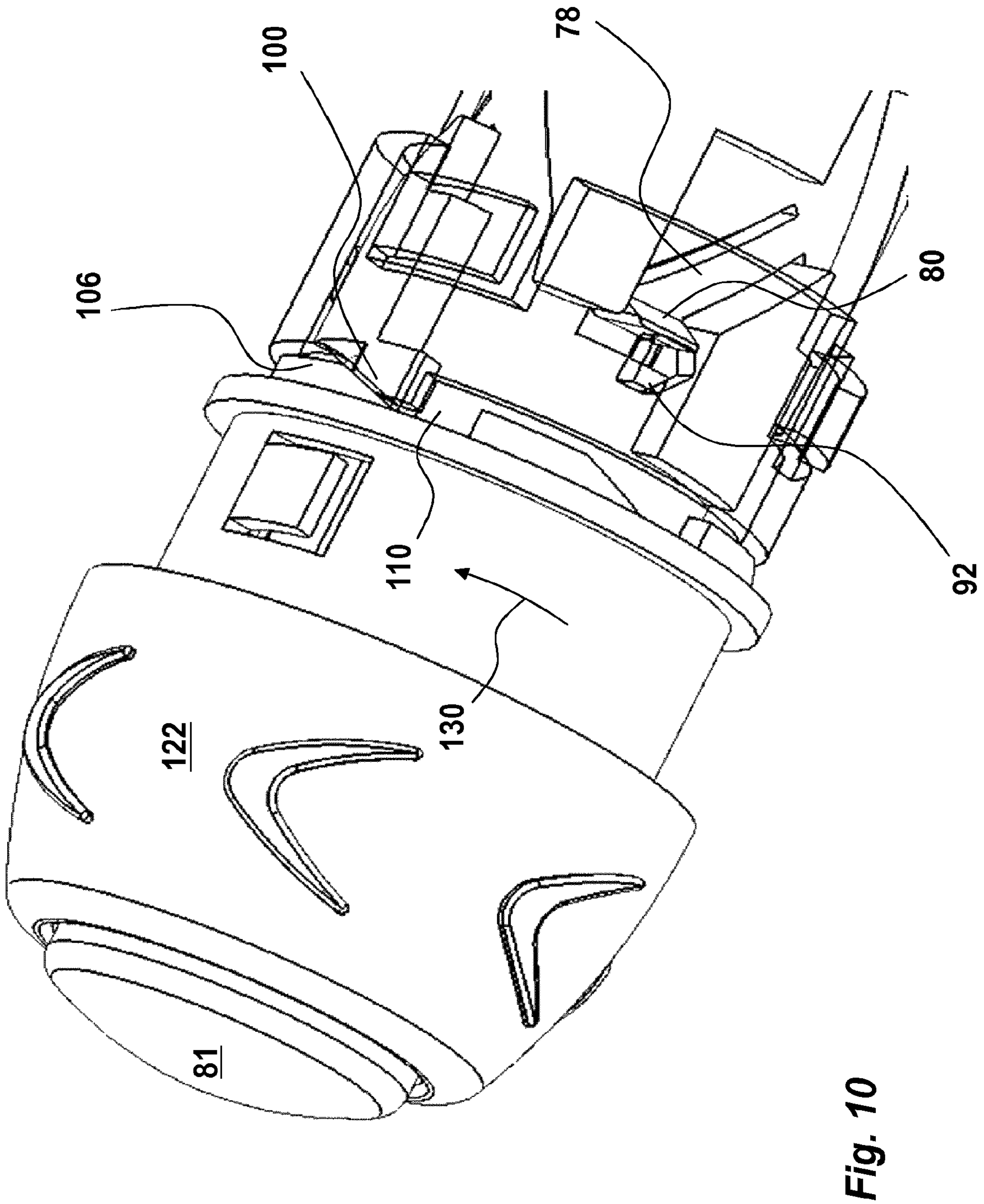

When delivered to a user, the biased actuator member 64 with its manual actuator 81 is inside the housing and inside the grip member 122 as seen in FIG. 10. More particularly, the transversal part of the manual actuator 81 is flush with the distal end of the manually movable activation member 102. This position of the biased actuator member 64 is due to that the at least one second guide element 92 of the actuator guide member 90 is in contact with the at least one wedge-shaped ledge 80 of the at least one lock element 78 of the biased actuator member 64. The at least one second guide element 92 is pressed against the at least one ledge 80 because of the spring means 82 urges the biased actuator member 64 in the distal direction. Further, the actuator guide member 90 and the manually movable activation member 102 are positioned such in relation to each other that the at least one first guide element 100 of the actuator guide member 90 is only partly in the space 110 between two third guide elements 106 of the manually movable activation member 102, as seen in FIG. 10.

Figure 11:
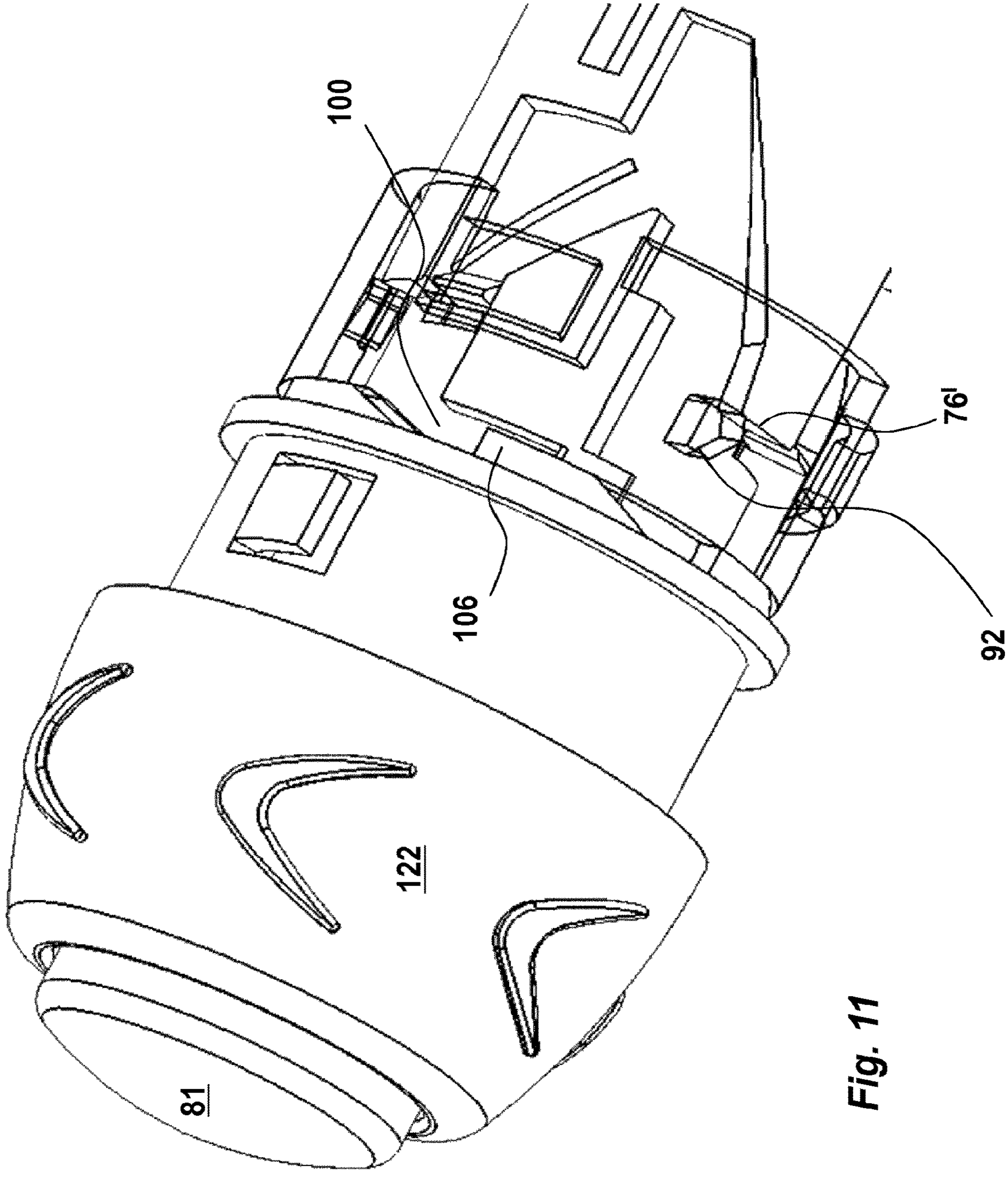

In order to activate the device, the manually movable activation member 102 is turned anti-clockwise in relation to the distal housing part as seen when viewing the device from its distal end and as shown by arrow 130 in FIG. 10 by a user gripping the grip member 122. The turning of the manually movable activation member 102 will cause at least one first guide element 100 of the actuator guide member 90 to fully enter the space 110 between two third guide elements 106 of the activator member 102 as seen in FIG. 11, whereby the actuator guide member 90 also will be turned in relation to the distal housing part. The manually movable activation member 102 is further prevented from being turned in the clock-wise direction due to the interaction between the tongues 116 and the protrusions 118.

Figure 12:
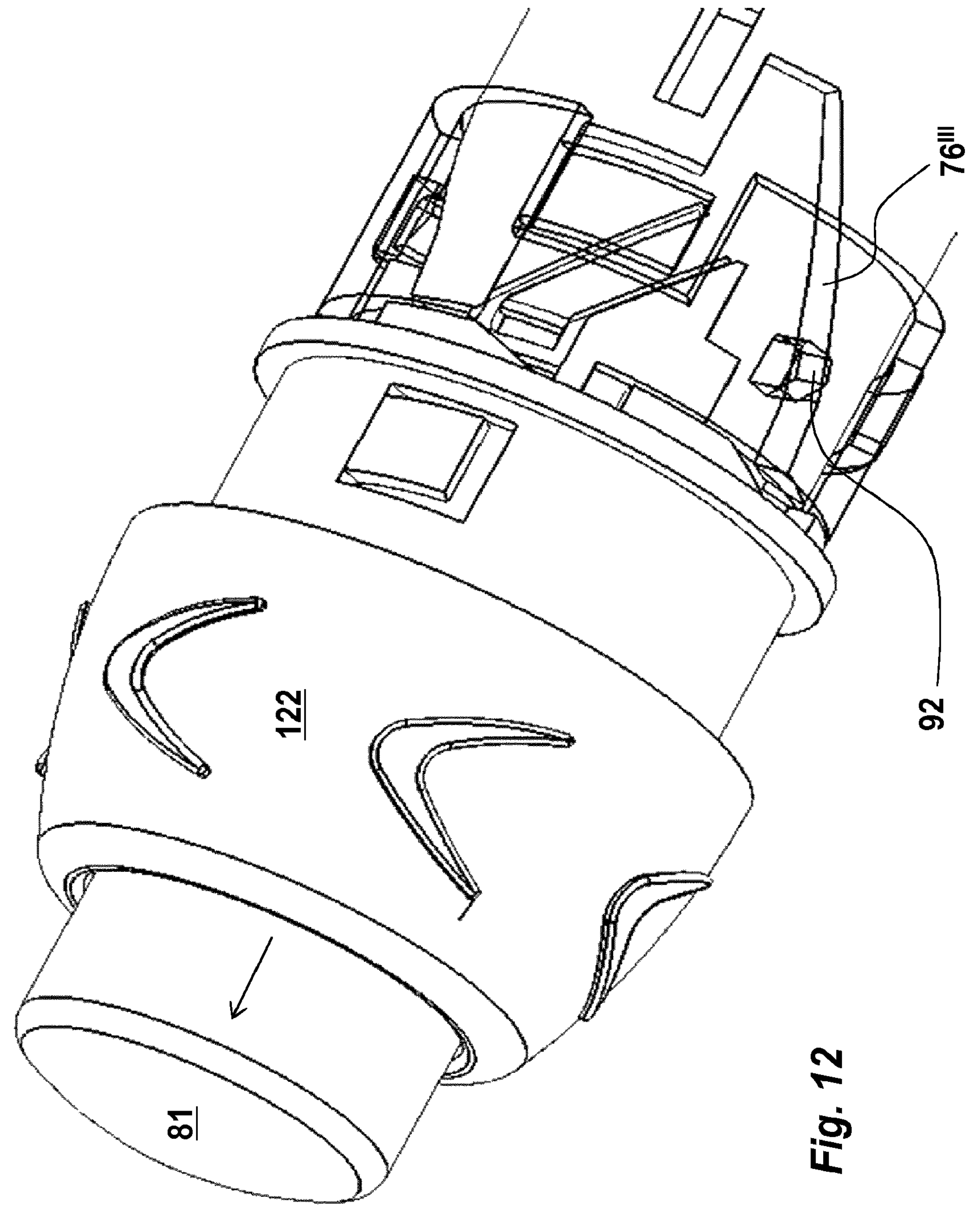
Figure 13:
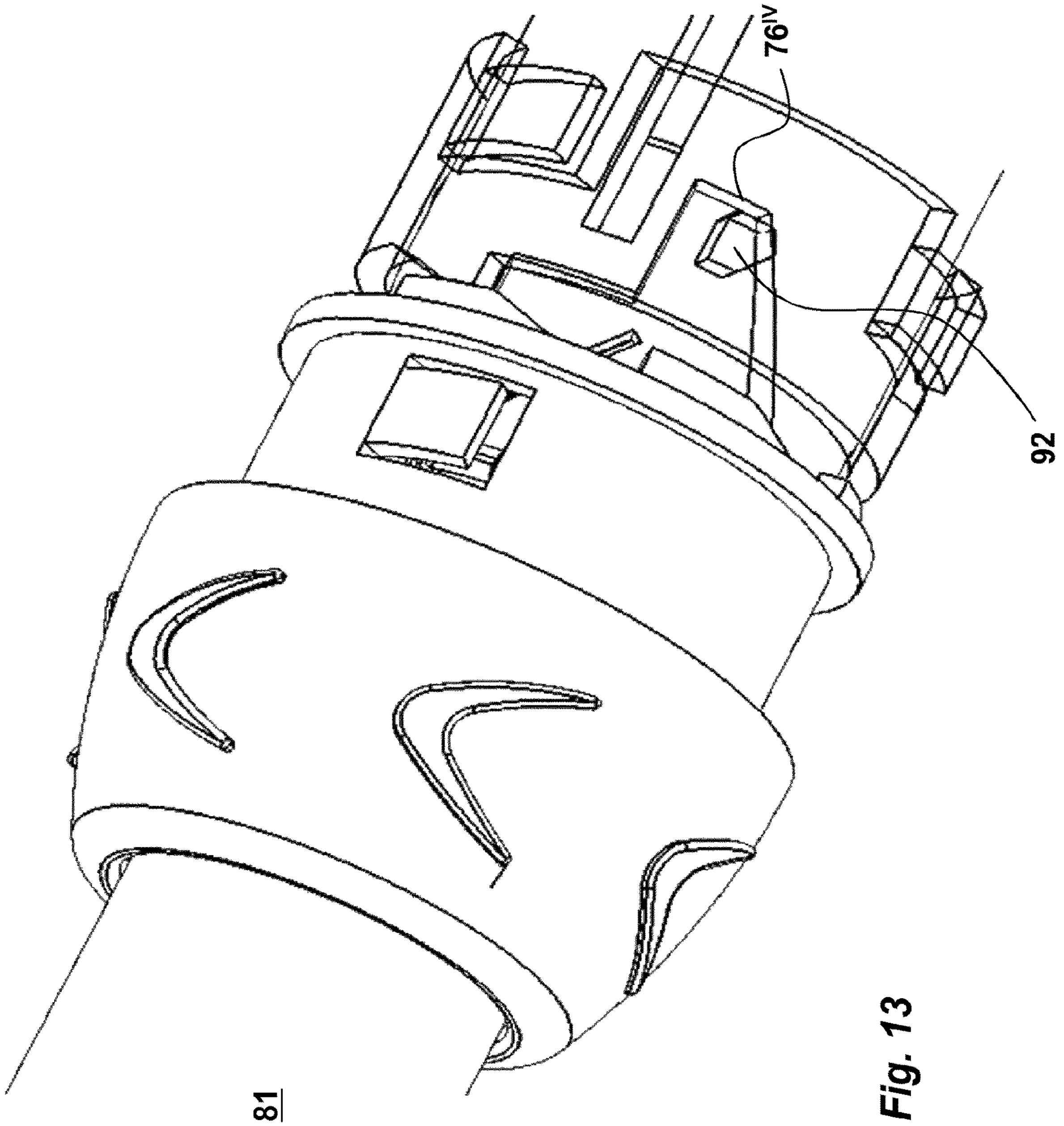

The turning of the actuator guide member 90 will cause the at least one second guide element 92 to first enter the guide surfaces 761 and then pass them, then further to pass along the guide surfaces $76^{II}$ and then the inclined surfaces $76^{III}$, FIG. 12. The force of the spring means 82 will now be able to force the biased actuator member 64 a predetermined distance from the distal end of the manually movable activation member such that the manual actuator 81 will extend out of from the distal end of the activator member 102, FIG. 12. Also, the longitudinally extending ledges 77 on the outer surface the biased actuator member 64 moves through the spaces formed between the radial inwardly extending protrusions 108 on the inner surface of the manually movable activation member 102 to reduce or minimize any play between the biased actuator member 64 and the manually movable activation member 102. The contact between the inclined surfaces $76^{III}$ and the at least one second guide element 92 will cause the actuator guide member 90 to be turned. The at least one first guide element 100 will then be moved out of the space 110 between the at least one third guide element 106 of the manually movable activation member 102, whereby the actuator guide member 90 is restricted to be rotated by the manually movable activation member 102. Further, the at least one second guide element 92 of the actuator guide member 90 are now in contact with the guide surface $76^{IV}$, FIG. 13, whereby the movement of the biased actuator member 64 is stopped with the manual actuator 81 in an extended position. Also, the longitudinally extending ledges 77 on the outer surface the biased actuator member 64 are now in contact with a distal internal flange of the manually movable activation member 102.

Figure 14:
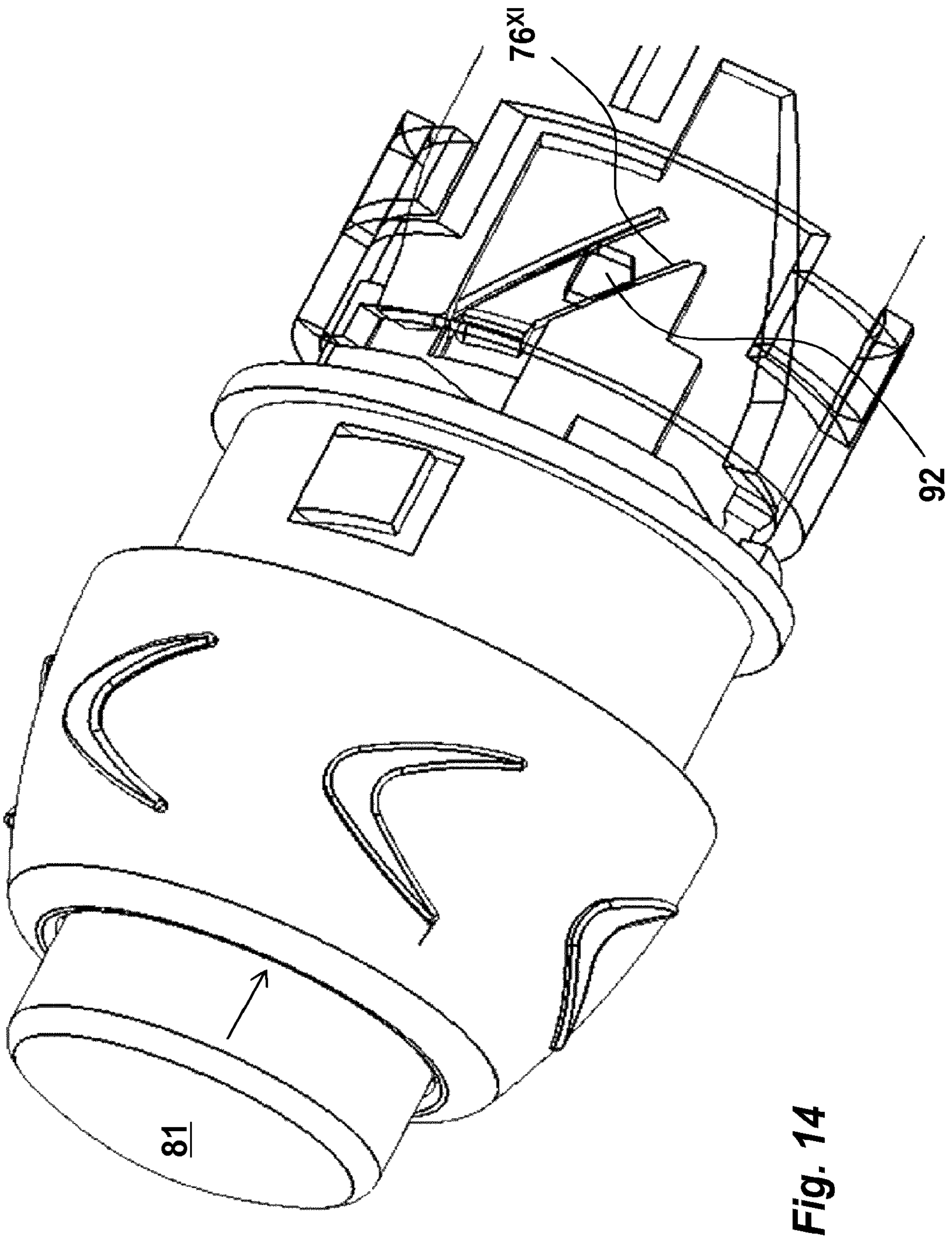

The device is now ready for dose delivery. The user then presses the proximal end of the device against a delivery site and in the case of an injection needle used as a medicament delivery member, a penetration is obtained. In order to deliver a predetermined amount of medicament, the user now presses on the manual actuator 81 of the biased actuator member 64 in the proximal direction. This causes the at least one second guide element 92 of the actuator guide member 90 to be moved in relation to the biased actuator member 64 such that the at least one second guide element 92 comes in contact with the inclined guide surface $76^{XI}$, FIG. 14, again causing the actuator guide member 90 to be turned. Further, the force from the inclined guide surface $76^{XI}$ will cause the at least one first guide element 100 of the actuator guide member 90 to move out of contact with the manually movable activation member 102.

Also, the movement of the biased actuator member 64 will cause the second driver 46 to be moved in the proximal direction. This movement will in turn cause the inclined surfaces 54 to act on the first set of protruding structures 44 of the first driver 34, whereby the first driver 34 will rotate due to the inclination of the surfaces 54. In turn, the rotation of the first driver 34 will cause the threaded plunger rod 24 to rotate due to the rotational lock between the two because of the ribs 38 and the grooves 36. When the threaded plunger rod 24 now rotates, it will be moved in the proximal direction due to the threaded connection between the threaded plunger rod 24 and the central passage 32 of the housing. Consequently, the proximal movement of the threaded plunger rod 24 will force the stopper 23 of the medicament container 20 in the proximal direction, whereby a predetermined amount of medicament will be delivered through the medicament delivery member.

Figure 15:
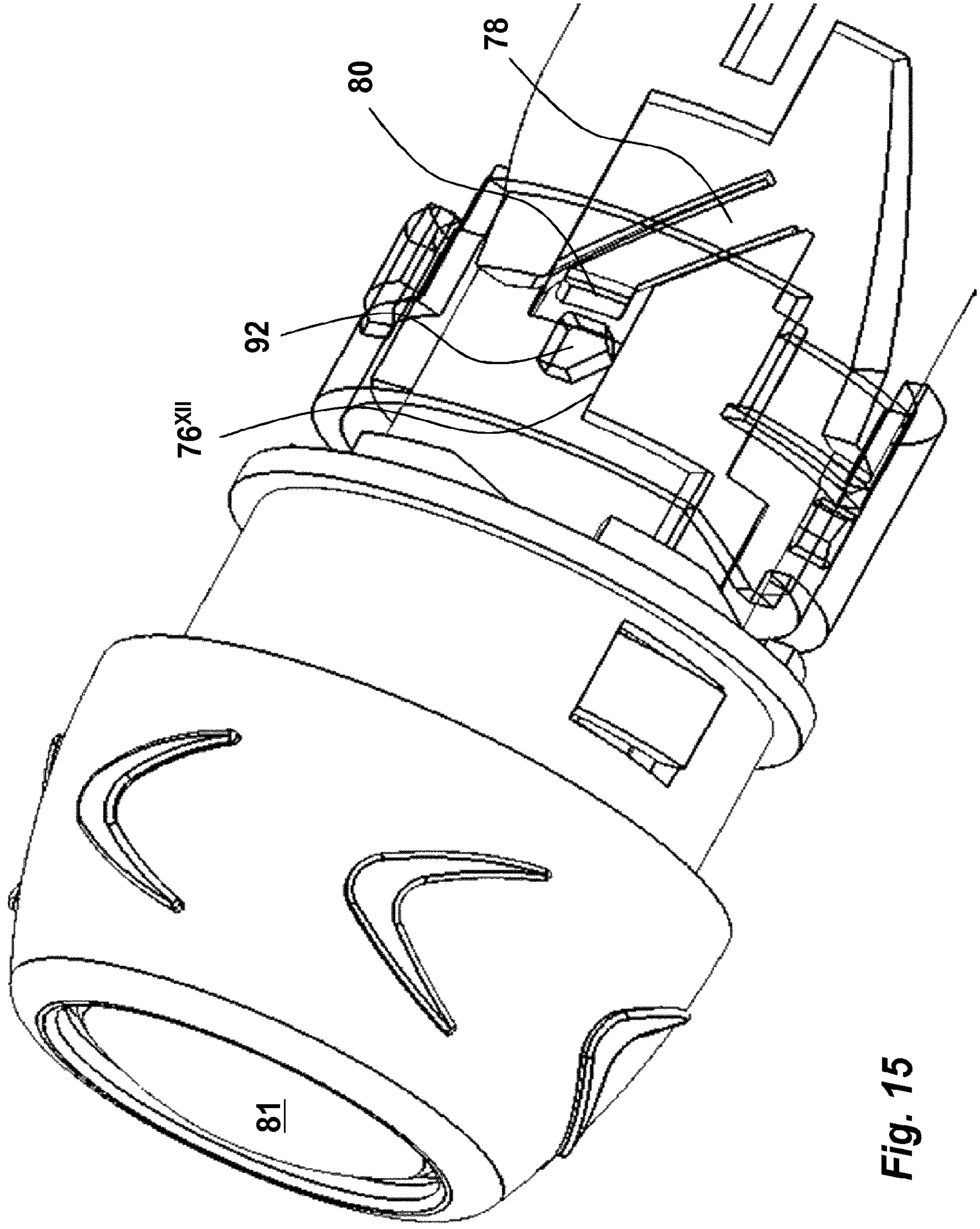

Further movement of the biased actuator member 64 in the proximal direction will cause the at least one second guide element 92 of the actuator guide member 90 to come in contact with the at least one wedge-shaped ledge 80 of the at least one lock element 78 whereby the at least one lock element 78 will flex inwards and the at least one second guide element 92 will pass the at least one wedge-shaped ledge 80, FIG. 15. The flexing of the at least one lock element 78 inwards is enabled by the cut-outs 58 in the second driver 46.

The passing of the at least one second guide element 92 will cause the at least one lock element 78 to flex back rapidly whereby the at least one ledge 80 will hit the inner surface of the actuator guide member 90, producing audible sounds, which sounds indicate that the delivery operation is completed. The biased actuator member 64 is now locked again in a depressed state.

Figure 16:
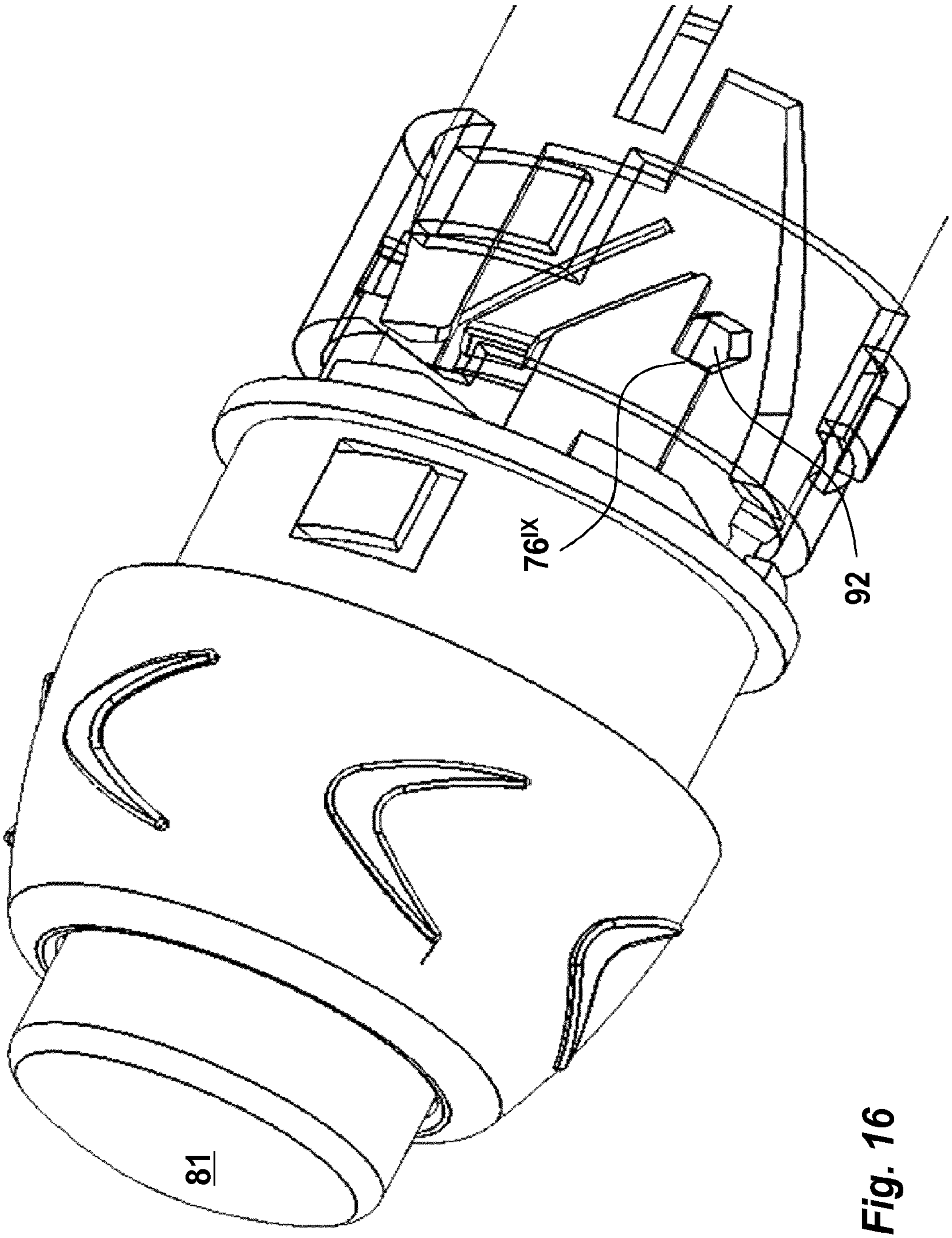

The present invention is arranged with a few safety features for preventing or minimizing delivery of wrong quantities of medicament if the device is handled in an inappropriate way. One feature handles the case if the user tries to press on the manual actuator too early, i.e. during the release of the biased actuator member 64 but before the biased actuator member 64 has moved such in the distal direction that it is fully extended and the at least one second guide element 92 are in contact with the surfaces $76^{IV}$, thus trying to press the manual actuator 81 before the device is ready to deliver a predetermined amount of medicament. In that case, the at least one second guide element 92 will move against the first blocking surface $76^{IX}$, FIG. 16, thereby blocking the biased actuator member 64 from movement in the proximal direction, indicating to the user to release the pressure on the manual actuator 81.

Figure 17:
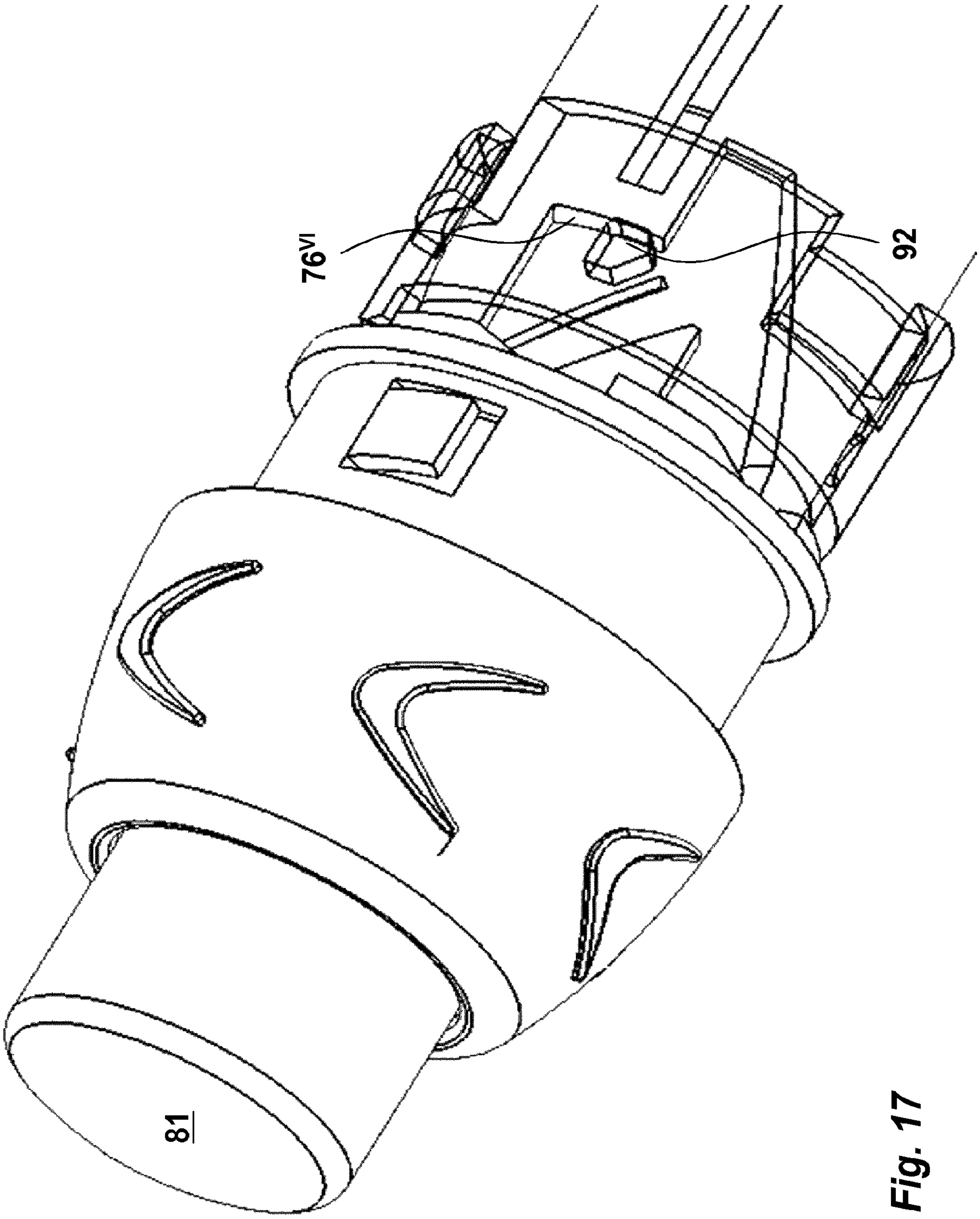

Another feature handles the case if the user during the pressing of the manual actuator 81 and thus the biased actuator member in the proximal direction when delivering a predetermined amount of medicament, suddenly releases the manual actuator 81, wherein only a part of the predetermined amount of medicament has been delivered. The spring means 82 will then try to force the biased actuator member 64 in the distal direction. However, this is prevented in that the at least one second guide element 92 will be moved in contact with the second blocking surface $76^{VI}$, FIG. 17, thereby preventing further movement. If not stopped, it would otherwise lead to the biased actuator member being again moved to a fully extended position, whereby it would be possible to deliver a new predetermined amount of medicament. This scenario is now prevented by the second blocking surfaces 76*v*.

It is to be understood that the embodiment described above and shown in the drawings is to be regarded only as a non-limiting example of the invention and that it may be modified in many ways within the scope of the patent claims.

The invention claimed is:

1. A medicament delivery device comprising:

a distal housing;

a proximal housing connected to the distal housing;

a first driver positioned within the distal housing and configured to rotate relative to the distal housing and the proximal housing;

a plunger rod rotatably fixed to the first driver, wherein the plunger rod rotates during delivery of medicament from a container positioned within the proximal housing;

a manually movable activation member positioned on a distally directed end surface of the distal housing, wherein the manually movable activation member is rotatable relative to the distal housing;

a biased actuator member configured to move distally a predetermined distance relative to the distal housing when the manually movable activation member is rotated;

an actuator guide member rotatably fixed to the manually movable activation member; and a lock element that locks the biased actuator member in a position within the distal housing to indicate a predetermined dose of medicament has been delivered, wherein the actuator guide member comprises a first guide element rotatably positioned in and relative to the distal housing, and wherein the actuator guide member comprises a second guide element configured to interact with a blocking surface located on a guide surface arranged on an outer circumferential surface of the biased actuator member when the biased actuator member moves proximally.

2. The device of claim 1, wherein the first guide element interacts with the manually movable activation member and the biased actuator member such that the actuator guide member is held in a position within the distal housing and is released from the held position after the dose of medicament is delivered.

3. The device of claim 1, wherein the interaction of the second guide element with the blocking surface prevents manual proximal movement of the biased actuator member during distal movement of the biased actuator member from a distal end of the manually movable activation member.

4. The device of claim 1, wherein the first guide element interacts with a corresponding guide element of the manually movable activation member when the manually movable activation member is moved axially.

5. The device of claim 1, wherein the plunger rod comprises an outer thread that is threadedly engaged with the distal housing.

6. The device of claim 5, wherein the first driver comprises a first set of protruding structures.

7. The device of claim 6, further comprising a second driver operatively engaged with the first driver such that movement of the biased actuator member through the predetermined distance is transformed into a rotational movement of the threaded plunger rod.

8. The device of claim 7, wherein the second driver comprises a set of inclined surfaces and a second set of protruding structures.

9. The device of claim 8, wherein when the biased actuator member is moved proximally the predetermined distance, the second set of protruding structures interacts with a corresponding set of protruding structures of the biased actuator member and the first set of protruding structures interacts with the set of inclined surfaces on the second driver.

10. The device of claim 1, wherein the biased actuator member is biased in a distal direction by a spring.

11. The device of claim 10, wherein one end of the spring abuts a proximally directed wall surface of the biased actuator member and another end of the spring abuts a circumferential ledge of a spring guide.

12. The device of claim 1, wherein the lock element produces an audible signal when the biased actuator member is locked into a position within the distal housing indicating the predetermined dose of medicament has been delivered.

13. The device of claim 12, wherein the lock element comprises a flexible tongue.

14. The device of claim 1, wherein the manually movable activation member includes a grip member arranged on an outer surface of the manually movable activation member.

15. The device of claim 1, wherein the biased actuator member includes a manual actuator extending from a distal end of the biased actuator member and extending through the manually movable activation member such that the manual actuator protrudes distally outward from a distal end of the manually movable activation member when the manually movable activation member is rotated causing the biased actuator member to move distally a predetermined distance relative to the distal housing.

16. The device of claim 15, wherein axial movement of the manual actuator relative to the distal housing in a proximal direction through the predetermined distance causes rotation of the plunger rod and a delivery of a dose of medicament from the container.

* * * * *